(12) United States Patent
Satoh

(10) Patent No.: US 12,728,238 B2
(45) Date of Patent: Sep. 8, 2026

(54) GUIDE WIRE

(71) Applicant: Asahi Intecc Co., Ltd., Seto (JP)

(72) Inventor: Fumitaka Satoh, Seto (JP)

(73) Assignee: ASAHI INTECC CO., LTD., Seto (JP)

( * ) Notice: Subject to any disclaimer, the term of this patent is extended or adjusted under 35 U.S.C. 154(b) by 527 days.

(21) Appl. No.: 18/201,185

(22) Filed: May 24, 2023

(65) Prior Publication Data

US 2023/0293859 A1 Sep. 21, 2023

Related U.S. Application Data

(63) Continuation of application No. PCT/JP2020/044007, filed on Nov. 26, 2020.

(51) Int. Cl.
*A61M 25/09* (2006.01)

(52) U.S. Cl.
CPC ... *A61M 25/09* (2013.01); *A61M 2025/09175* (2013.01); *A61M 2025/09191* (2013.01)

(58) Field of Classification Search
CPC ........ A61M 25/09; A61M 2025/09175; A61M 2025/09191; A61M 2025/09083; A61M 2025/09091; A61M 2025/09108; A61M 2025/09058; A61M 2025/09166
See application file for complete search history.

(56) References Cited

U.S. PATENT DOCUMENTS 6,348,041 B1 * 2/2002 Klint ..................... A61M 25/09 600/585
8,715,227 B2 * 5/2014 Kontos .......... A61B 17/320725 606/159
2004/0116833 A1 6/2004 Kato et al.
2009/0005706 A1 1/2009 Miyata et al.
2015/0238734 A1 8/2015 Kanazawa
(Continued)

FOREIGN PATENT DOCUMENTS

JP 2002-539901 A 11/2002
JP 2004-190167 A 7/2004
(Continued)

OTHER PUBLICATIONS

International Search Report and Written Opinion mailed on Jan. 19, 2021, received for PCT Application PCT/JP2020/044007, filed on Nov. 26, 2020, 9 pages including English Translation.

*Primary Examiner* — Charles A Marmor, II
*Assistant Examiner* — Severo Antonio P Lopez
(74) *Attorney, Agent, or Firm* — XSENSUS LLP

(57) ABSTRACT

A guide wire includes a core shaft and a twisted wire coil body having a plurality of wires twisted together and arranged along an outer periphery of the core shaft. The twisted wire coil body includes a distal end portion including a distal end and a feature portion, and a proximal end portion, and has a smaller outer diameter in the feature portion than at the proximal end portion. Among the plurality of wires, an outermost wire having a longest distance to a center point of the core shaft in a transverse cross section of the twisted wire coil body in the feature portion, has a smaller cross-sectional area than a wire having a longest distance to the center point in a transverse cross section of the twisted wire coil body at the proximal end portion. An inner diameter of the twisted wire coil body is constant.

19 Claims, 5 Drawing Sheets

(56) References Cited

U.S. PATENT DOCUMENTS

| | | | | |
|---|---|---|---|---|
| 2016/0089514 | A1* | 3/2016 | Shimizu | A61M 25/09 604/528 |
| 2017/0095314 | A1* | 4/2017 | Baldwin | A61M 25/09 |
| 2017/0259040 | A1 | 9/2017 | Furukawa | |
| 2020/0147352 | A1* | 5/2020 | Zheng | A61M 25/09 |

FOREIGN PATENT DOCUMENTS

| | | | |
|---|---|---|---|
| JP | 2007-135645 | A | 6/2007 |
| JP | 2009-000337 | A | 1/2009 |
| JP | 2011-177392 | A | 9/2011 |
| JP | 5473677 | B2 | 4/2014 |
| JP | 2015-171519 | A | 10/2015 |
| WO | 00/57944 | A1 | 10/2000 |
| WO | 2017/154164 | A1 | 9/2017 |

* cited by examiner 100
44
II
SI
SO
30
BP
IIIA
IIIB
13
DP
10
12
AP
IIIC
11
FP
50
42
DI
DE
Y
X
Z Y
X
300X
331
(A1)
332
333
330
334
335
336
310
D1
DA
300X
(30)
330
310
100
VL
PO
300(30)
SO
SI
300
(30)
DF
DE
DI
DF
RD
O
H
10
IC
OC 100A
44
II
II
SI
SO
BP
30A
ⅢA
ⅢA
ⅢB
ⅢB
13
DP
10
12
AP
ⅢC
ⅢC
FP
11
HP
50
42A
DI
DE
Y
X
Z

GUIDE WIRE

CROSS REFERENCE TO RELATED APPLICATION

This application is a continuation application of International Application No. PCT/JP2020/044007 filed Nov. 26, 2020, the entire contents of which is incorporated herein by reference.

TECHNICAL FIELD

The technique disclosed herein relates to a guide wire to be inserted into a blood vessel or the like.

BACKGROUND ART

A method using a catheter is widely used for a method for treating or inspecting a constricted portion or an occluded portion (hereinafter referred to as "lesion") in a blood vessel or the like. Typically, a guide wire is used to guide a catheter to a lesion in a blood vessel or the like. A guide wire includes a core shaft and a coil body arranged to surround an outer periphery of the core shaft. For example, a rotational performance to transmit a rotational force applied to a proximal end side portion of the guide wire to a distal end portion and good flexibility in the distal end side portion of the guide wire are required for the guide wire. For a purpose such as arranging a component allowing for application of various types of performances to the guide wire, an inner cavity is formed between the core shaft and the coil body.

In the coil body configured of a solid wire (single wire) of a conventional guide wire, when an inner diameter of the coil body is maintained constant and an outer peripheral surface of the coil body at the distal end side of the guide wire is ground, the guide wire is formed so that an outer diameter of the guide wire is smaller toward the distal end side (see Patent Literature 1, for example). There is also known a guide wire including a twisted wire coil body configured of a twisted wire obtained by twisting a plurality of wires (see, for example, Patent Literature 2).

CITATION LIST

Patent Literature

Patent Literature 1: Translation of Japanese Unexamined Patent Application Publication No. 2002-539901

Patent Literature 2: Japanese Unexamined Patent Application Publication No. 2009-000337

SUMMARY

Technical Problems

In the conventional guide wire formed so that the outer diameter of the guide wire is smaller toward the distal end side, the single wire configuring the coil body is thinner at the distal end side, and thus, there is room for improvement in terms of rotational performance. On the other hand, the guide wire including the twisted wire coil body configured of the twisted wire may have an improved rotational performance, but a plurality of wires configuring the twisted wire interfere with one another to deteriorate the flexibility. In the guide wire including the twisted wire coil body, when a diameter of each wire configuring the twisted wire is reduced, the flexibility is improved, but the rotational performance may possibly deteriorate. When the conventional twisted wire is used to wind the twisted wire so that the outer diameter of the twisted wire coil body at the distal end side is small, the inner diameter of the twisted wire coil body is also small, and thus, it is difficult to secure the inner cavity formed with the core shaft. Thus, there is a need in the guide wire that the inner cavity formed between the core shaft and the coil body is secured, and at the same time, a good flexibility of the distal end portion of the guide wire is maintained and the rotational performance is improved.

The present specification discloses a technique by which it is possible to solve at least one of the above-described and other problems.

Solution to Problem

The techniques disclosed herein can be realized in the following aspects, for example.

(1) A guide wire disclosed in the present specification includes a core shaft and a twisted wire coil body configured of a twisted wire obtained by twisting a plurality of wires and arranged to surround an outer periphery of the core shaft, the twisted wire coil body including a distal end portion including a distal end and a feature portion, and a proximal end portion, in which an outer diameter of the twisted wire coil body in the feature portion is smaller than an outer diameter of the twisted wire coil body at the proximal end portion, a cross-sectional area of an outermost wire being a wire having a longest distance to a center point of the core shaft, out of the plurality of wires, in a transverse cross section of the twisted wire coil body in the feature portion, is smaller than a cross-sectional area of the wire having a longest distance to the center point of the core shaft, out of the plurality of wires, in a transverse cross section of the twisted wire coil body at the proximal end portion, and an inner diameter of the twisted wire coil body is constant.

When the cross-sectional area of the twisted wire coil body in the transverse cross section of the guide wire is smaller, the flexibility is improved. In the present guide wire, the inner diameter of the twisted wire coil body is constant, and the outer diameter of the twisted wire coil body in the feature portion is smaller than the outer diameter of the twisted wire coil body at the proximal end portion. In other words, in the transverse cross section of the guide wire, the cross-sectional area of the twisted wire coil body in the feature portion is smaller than the cross-sectional area of the twisted wire coil body at the proximal end portion. Therefore, compared to the proximal end portion, it is possible to improve the flexibility of the twisted wire coil body in the feature portion, and therefore, it is possible to improve the flexibility of the guide wire.

The rotational performance of the guide wire is improved as the diameter of each wire of the twisted wire forming the twisted wire coil body is increased. In the present guide wire, in the transverse cross section of the twisted wire coil body in the feature portion, the cross-sectional area of an outermost wire of the plurality of wires configuring the twisted wire is smaller than the cross-sectional area of an outermost wire in the transverse cross section of the twisted wire coil body at the proximal end portion. That is, in the present guide wire, it is possible to decrease the outer diameter of the twisted wire coil body without evenly decreasing the diameter of each one of the wires configuring the twisted wire coil body over the entire twisted wire coil body. Thus, it is possible to reduce a deterioration of the rotational performance of the guide wire. In the present guide wire, the inner diameter of the twisted wire coil body is made constant, thus it is possible to secure an inner cavity formed between the core shaft and the coil body. Therefore, according to the present guide wire, it is possible to secure the inner cavity formed between the core shaft and the coil body, and at the same time, it is possible to maintain a good flexibility of the distal end portion of the guide wire and to improve the rotational performance.

(2) In the above-described guide wire, the configuration may be such that in at least one transverse cross section of the twisted wire coil body in the feature portion, the outermost wire forming the feature portion has a gap with an adjacent one of the wires. To improve the operability of the guide wire in a complicatedly curved blood vessel, there is a case where the guide wire is used by using a fingertip or an instrument (a shape needle, for example) to bend the distal end portion of the guide wire, or to return such a distal end portion to the original shape after use (hereinafter, referred to as "shape and reshape"). Thus, the distal end portion of the guide wire may be required to be easily shaped and reshaped. In the guide wire having the present configuration, the outermost wire configuring the feature portion has a gap between an adjacent one of the wires. Thus, as compared to a configuration not including the gap, it is possible to prevent interference between the wires, and it is possible to improve the easiness and the flexibility when shaping and reshaping the twisted wire coil body in the feature portion. Therefore, according to the guide wire having such a configuration, the ease of the shaping and reshaping of the guide wire and and the flexibility of the guide wire may be improved.

(3) In the above-described guide wire, the configuration may be such that, in the transverse cross section of the twisted wire coil body in the feature portion, an outermost surface of surfaces forming the outermost wire has a flat shape. In other words, the guide wire of such a configuration has a flat surface on the outer peripheral surface of the twisted wire coil body in the feature portion. Thus, as compared to a configuration where the outer peripheral surface has an arc shape, it is possible to ensure that the fingertip or the instrument (the shape needle, for example) is in surface contact with the flat surface of the outer peripheral surface, and it is possible to improve the easiness of the shaping and reshaping of the twisted wire coil body in the feature portion. Therefore, according to the guide wire having such a configuration, the ease of shaping and reshaping of the guide wire may be improved.

(4) In the above-described guide wire, the configuration may be such that the feature portion includes, at a side of the proximal end portion, a portion where the cross-sectional area of the outermost wire continuously decreases in size toward the distal end from the side of the proximal end portion. In the guide wire having the present configuration, the stiffness of the twisted wire coil body gradually decreases in the portion where the cross-sectional area of the outermost wire in the feature portion continuously decreases. According to the guide wire having the present configuration, such a portion is included at the side of the proximal end portion in the feature portion, and thus, it is possible to suppress deterioration of rotational performance features such as torqueability and rotation followability due to a sudden change in stiffness between the feature portion and the proximal end portion.

(5) In the above-described guide wire, the configuration may be such that the proximal end portion of the twisted wire coil body is integrally formed with the feature portion. In a configuration where the proximal end portion of the twisted wire coil body and the feature portion are joined with a joint portion, the rotational force transmitted from the proximal end portion is not smoothly transmitted to the feature portion, and due to a residual stress in the joint portion, rotational performance features such as torqueability and rotation followability are deteriorated. On the other hand, according to the guide wire of the present configuration, the proximal end portion of the twisted wire coil body and the feature portion are integrally formed, and thus, the rotational force may be transmitted from the proximal end portion to the feature portion, improving the rotational performance of the guide wire.

(6) In the above-described guide wire, the configuration may be such that a surface roughness of the outermost surface of the outermost wire in the feature portion is higher than a surface roughness of an inner peripheral surface of the twisted wire coil body in the feature portion. According to the guide wire having the present configuration, in a configuration where an outer peripheral surface of the guide wire is covered with resin, a surface area of the outer peripheral surface of the twisted wire coil body increases, and thus, adhesion between the outer peripheral surface and the resin may be improved and peeling of the resin from the coil body may be suppressed, and the like.

The techniques disclosed herein can be achieved by various aspects, for example, in aspects such as a guide wire and a method of manufacturing the guide wire.

DETAILED DESCRIPTION

A. First Embodiment

A-1. Basic Configuration of Guide Wire 100

Figure 1:
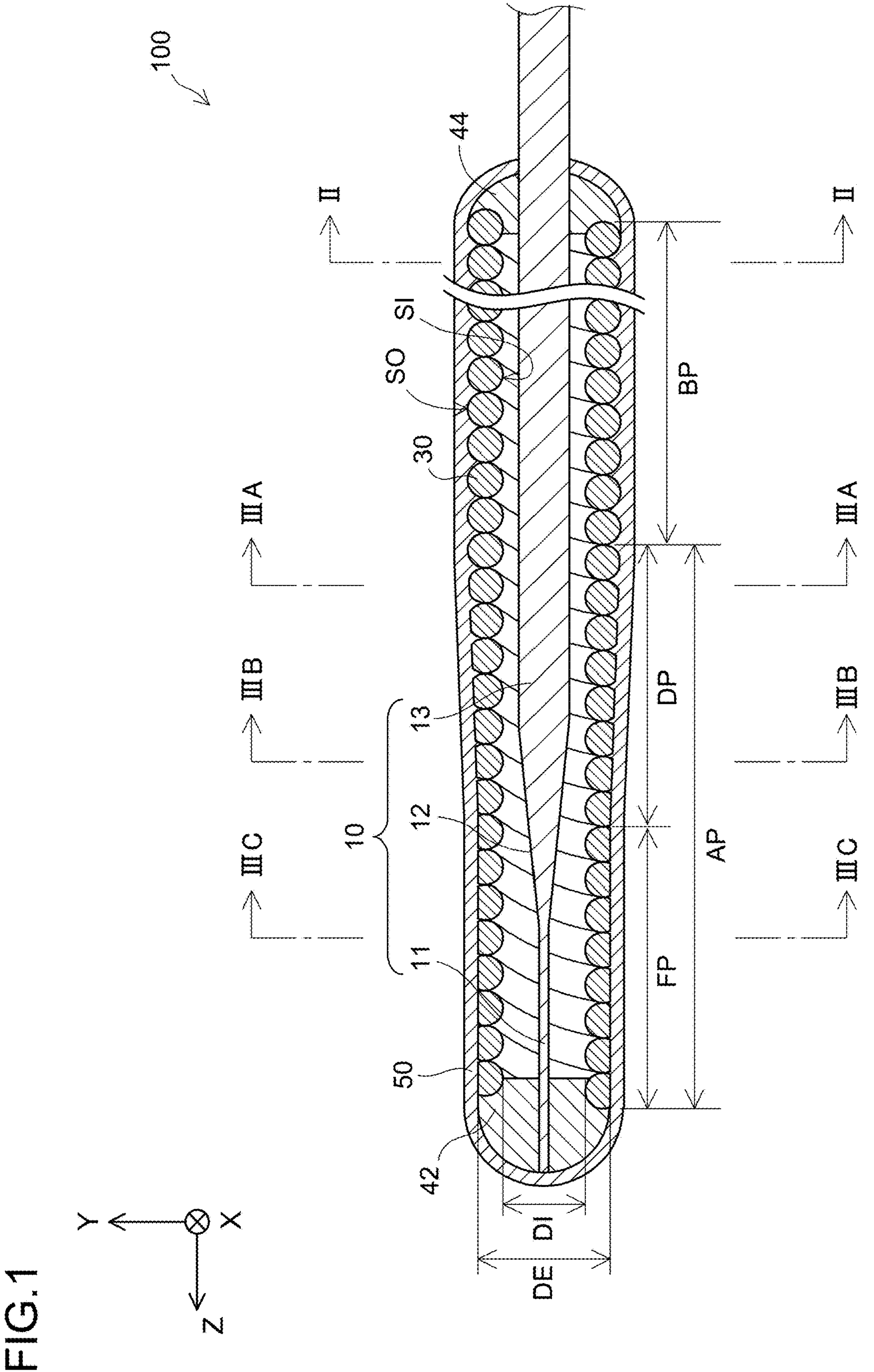
FIG. 1 is an explanatory diagram schematically illustrating a configuration of a guide wire 100 in a first embodiment.
Figure 2:
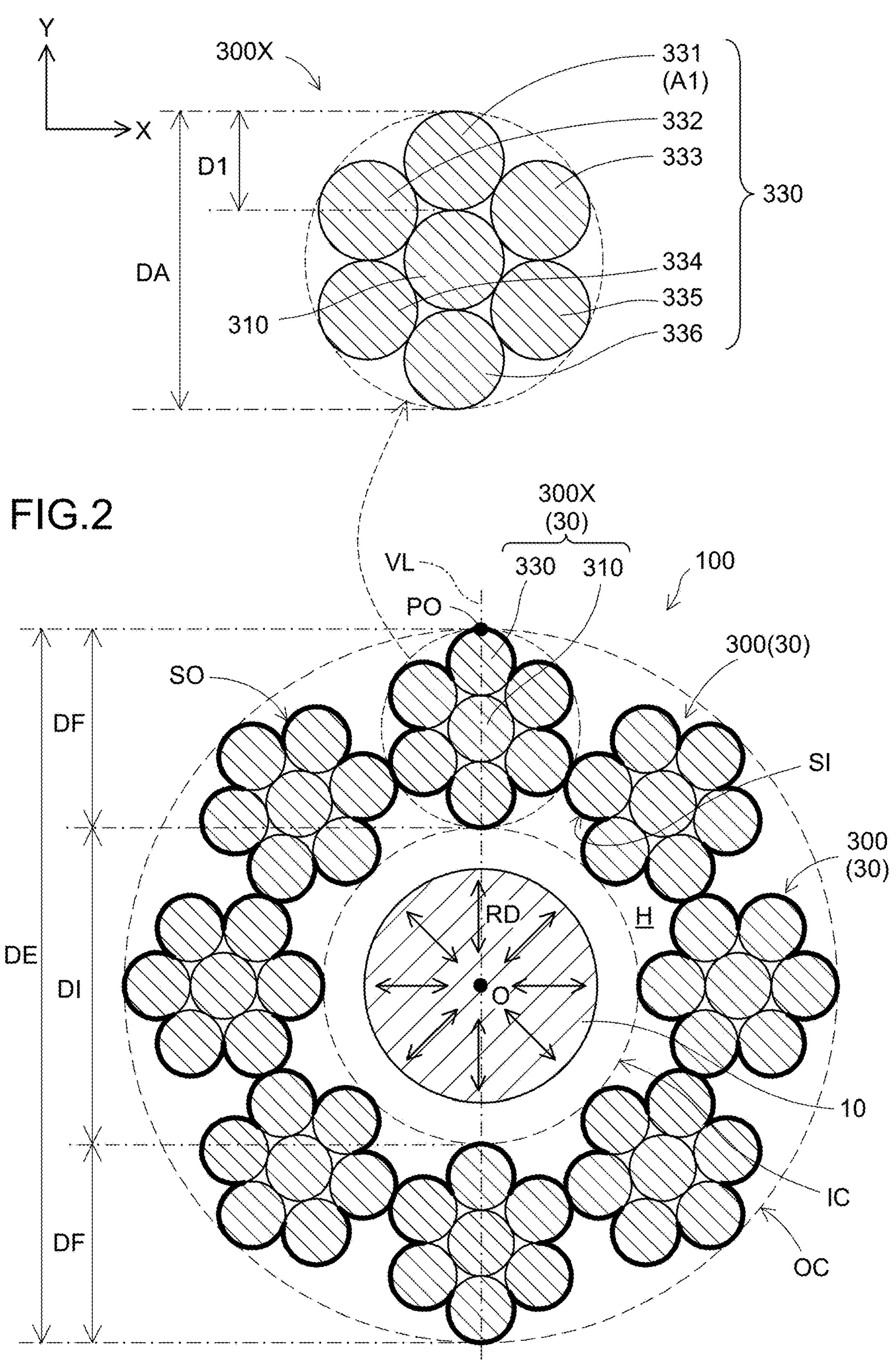
FIG. 2 is an explanatory view schematically illustrating an XY cross-sectional configuration of the guide wire 100 in FIG. 1.
Figure 3:
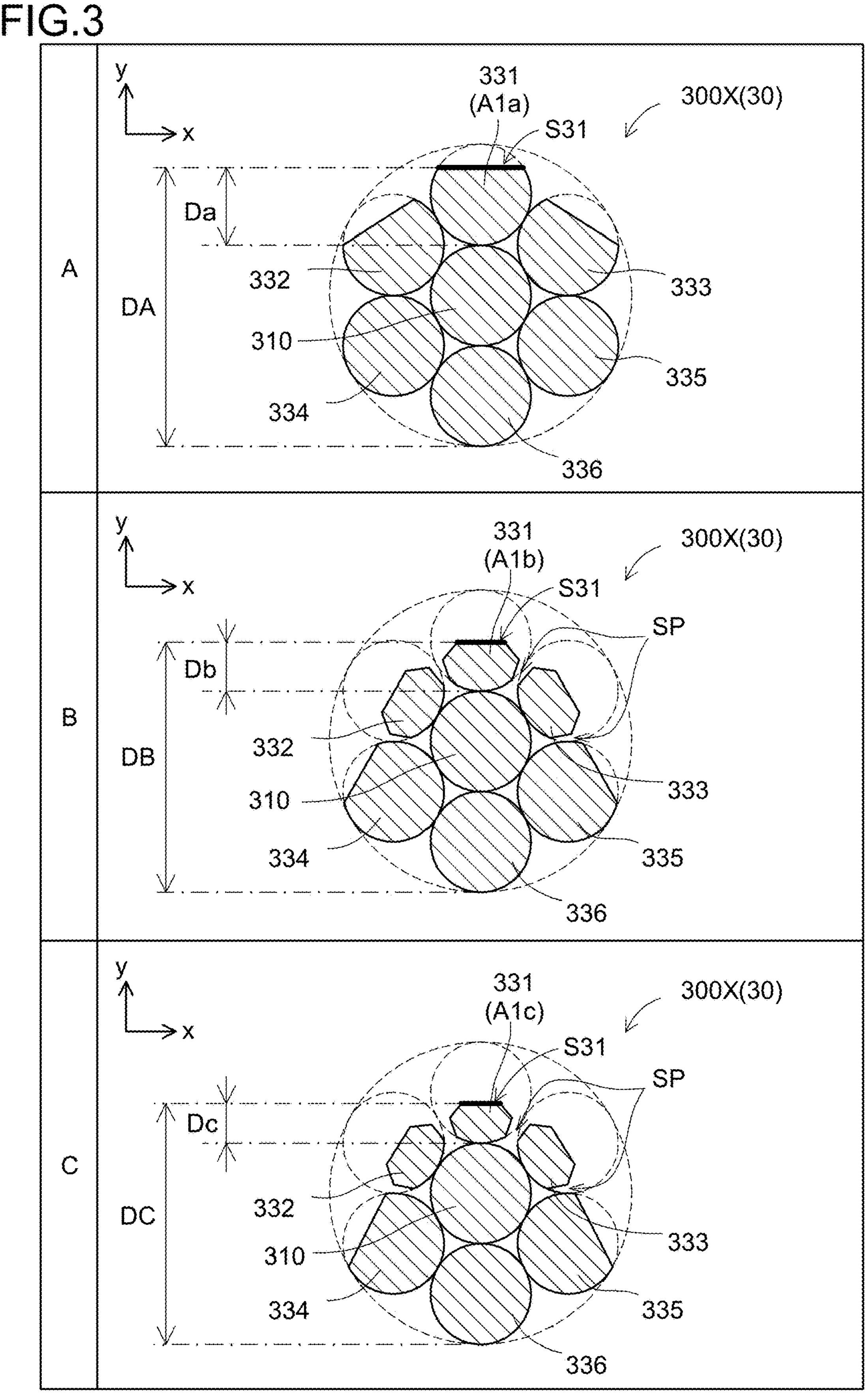
FIG. 3 is an explanatory view schematically illustrating XY cross-sectional configurations of the guide wire 100 in FIG. 1.

FIGS. 1, 2, and 3 are explanatory diagrams each schematically illustrating a configuration of a guide wire 100 in the present embodiment. FIG. 1 illustrates the configuration of a longitudinal cross section (YZ cross section) of the guide wire 100, and FIG. 2 illustrates the configuration of a transverse cross section (XY cross section) of the guide wire 100 at a position II-II in FIG. 1. Sections A, B, and C in FIG. 3 illustrate configurations of transverse cross sections (XY cross sections) of the guide wire 100 taken at positions IIIA-IIIA, IIIB-IIIB, and IIIC-IIIC in FIG. 1, respectively. In FIG. 1, not all of the guide wire 100 is illustrated. In FIG. 1, a Z-axis positive direction side is a distal end side (far side) to be inserted into a body, and a Z-axis negative direction side is a proximal end side (near side) operated by a technician such as a doctor. FIG. 1 illustrates a state where the guide wire 100 has an overall linear shape substantially parallel to the Z-axis direction, however, the guide wire 100 has enough flexibility to be bent relative to the Z-axis.

In this specification, for convenience of explanation, the guide wire 100 is presumed to be in the state illustrated in FIG. 1, and the Z-axis direction is referred to as an "axial direction of the guide wire 100" or simply the "axial direction", and a direction of rotation about the Z axis is referred to as a "circumferential direction of the guide wire 100" or simply the "circumferential direction".

The guide wire 100 is a long medical device to be inserted into a blood vessel or the like to guide a catheter to a lesion (a constricted portion or an occluded portion) in a blood vessel or the like. The total length of the guide wire 100 is, for example, about 1500 mm to 3000 mm, and the outer diameter of the guide wire 100 is, for example, about 0.5 to 1.2 mm.

The guide wire 100 includes a core shaft 10, a coil body 30, a distal end side joint portion 42, a proximal end side joint portion 44, and a resin portion 50.

The core shaft 10 is a long member having a small diameter on the distal end side and a large diameter on the proximal end side. More specifically, the core shaft 10 includes a small diameter portion 11 having a rod shape, a large diameter portion 13 being located on the proximal end side with respect to the small diameter portion 11 and having a rod shape having a larger diameter than the small diameter portion 11, and a tapered portion 12 located between the small diameter portion 11 and the large diameter portion 13 and whose diameter gradually increases going from a boundary location with the small diameter portion 11 toward a boundary location with the large diameter portion 13. A shape of the transverse cross section (XY cross section) at each position of the core shaft 10 can take any shape, and is, for example, a circular shape or a flat plate shape. The outer diameter of the large diameter portion 13 is, for example, about 0.2 to 0.6 mm.

A well-known material is used as a material to form the core shaft 10; for example, a metal material, and more specifically stainless steel (SUS302, SUS304, SUS316, and the like), a superelastic alloy such as a Ni—Ti alloy a piano wire, a nickel-chromium alloy a cobalt alloy tungsten, and the like is used. The core shaft 10 may be entirely formed of the same material, or may be configured of different materials for each portion.

As illustrated in FIGS. 1 and 2, the coil body 30 is a coil-shaped member formed into a hollow cylindrical shape by winding a plurality of twisted wires 300 into a spiral shape, and is arranged to surround an outer periphery of the core shaft 10. An inner cavity H is formed between the core shaft 10 and the coil body 30. In the present embodiment, the coil body 30 has a configuration in which eight of the twisted wires 300 are tightly wound. The coil body 30 includes a proximal end portion BP and a distal end portion AP including a distal end of the coil body 30. The coil body 30 is an example of a twisted wire coil body in the claims, and the distal end portion AP is an example of a distal end portion and a feature portion in the claims. A configuration of the coil body 30 will be described in detail later.

A well-known material is used as a material to form the coil body 30; for example, a metal material, and more specifically, stainless steel (SUS302, SUS304, SUS316, and the like), a superelastic alloy such as a Ni—Ti alloy, a piano wire, a nickel-chromium alloy, a cobalt alloy, tungsten, and the like is used. The plurality of twisted wires 300 may be formed of the same material, and may be formed of different materials. A core wire 310 and side wires 330 configuring the twisted wire 300, which will be described later, may be formed of the same material, and may be formed of different materials.

The distal end side joint portion 42 is a member that joins a distal end of the core shaft 10 and a distal end of the distal end portion AP (specifically a flat portion FP) of the coil body 30. That is, the distal end of the core shaft 10 and the distal end of the distal end portion AP of the coil body 30 are tightly fixed to be embedded into the distal end side joint portion 42. An outer peripheral surface of the distal end side joint portion 42 on the distal end side is a smooth surface (for example, a substantially hemispherical surface). The proximal end side joint portion 44 is a member that joins the core shaft 10 and a proximal end of the proximal end portion BP of the coil body 30, at a predetermined position between the proximal end and the distal end of the core shaft 10 along the axial direction. That is, the proximal end of the proximal end portion BP of the coil body 30 is tightly fixed to be embedded into the proximal end side joint portion 44.

Well-known materials may be used for the distal end side joint portion 42 and the proximal end side joint portion 44, and for example, a brazing material (such as aluminum alloy brazing, silver brazing, and gold brazing), metal solder (such as Ag—Sn alloy and Au—Sn alloy), an adhesive (such as an epoxy-based adhesive), and the like are used. In the present embodiment, a brazing material is used as the material forming the distal end side joint portion 42 and the proximal end side joint portion 44.

The resin portion 50 is a coating member formed of a resin and covering the outer peripheral surfaces of the coil body 30, the distal end side joint portion 42, and the proximal end side joint portion 44. A well-known material may be used as for the resin portion 50, and examples thereof include polyurethane, polyethylene, polyvinyl chloride, polyester, polypropylene, polyamide, polyimide, polyvinyl propylene; fluorine-based resins such as PTFE; and silicone resins. A thickness of the resin portion 50 is from about 0.01 to 0.1 mm, for example.

A-2. Detailed Configuration of Coil Body 30

Next, a configuration of the coil body 30 in the guide wire 100 of the present embodiment will be described in detail. As described above, the coil body 30 of the guide wire 100 of the present embodiment is configured of the plurality of twisted wires 300 and includes the proximal end portion BP and the distal end portion AP. Each of the plurality of twisted wires 300 configuring the coil body 30 is continuous from the proximal end portion BP to the distal end portion AP. In other words, the proximal end portion BP and the distal end portion AP are integrally formed. An outer diameter DE of the coil body 30 at the distal end portion AP is smaller than an outer diameter DE of the coil body 30 at the proximal end portion BP. On the other hand, an inner diameter DI of the coil body 30 is substantially constant across both the proximal end portion BP and the distal end portion AP. An outer diameter DF of the twisted wire 300 is, for example, approximately from about 0.1 to 0.4 mm. The outer diameter DE is a diameter of a circumscribed circle OC of the coil body 30, and the inner diameter DI is a diameter of an inscribed circle IC of the coil body 30. The outer diameter DF of the twisted wire 300 is a length in a radial direction RD of the core shaft 10.

The distal end portion AP is configured of a diminishing portion DP and the flat portion FP. The diminishing portion DP is a portion that continues to the proximal end portion BP, and the flat portion FP is a portion that continues to the diminishing portion DP and includes the distal end of the coil body 30. In the diminishing portion DP, the outer diameter DE of the coil body 30 continuously decreases in size from the proximal end side to the distal end side. On the other hand, in the flat portion FP, the outer diameter DE of the coil body 30 is substantially constant across the proximal end side and the distal end side. That is, the outer diameter DE at the proximal end side of the diminishing portion DP is equivalent to the outer diameter DE at the distal end side of the proximal end portion BP, and the outer diameter DE at the proximal end side of the flat portion FP is equivalent to the outer diameter DE at the distal end side of the diminishing portion DP. The diminishing portion DP is an example of "a portion in which a cross-sectional area of an outermost wire continuously decreases from a side of a proximal end portion to a distal end" in the claims.

With reference to FIG. 2, the twisted wires 300 configuring the coil body 30 will be described. FIG. 2 illustrates a transverse cross section of the coil body 30 at the proximal end portion BP (hereinafter also simply referred to as "transverse cross section of the proximal end portion BP"). The transverse cross section of the coil body 30 illustrated in FIG. 2 is an example of a transverse cross section of the coil body 30, and the coil body 30 may have a configuration different from the configuration illustrated in the transverse cross section of the coil body 30 illustrated in FIG. 2 in other transverse cross sections. One of the twisted wires 300 from among the twisted wires 300 configuring the coil body 30 (hereinafter referred to as "specific twisted wire 300X") will be described below, and the twisted wires 300 other than the specific twisted wire 300X are configured in much the same way as the specific twisted wire 300X. The specific twisted wire 300X has a two-layer structure in which the core wire 310 and the side wires 330 (hereinafter, the core wire 310 and the side wires 330 may be collectively referred to as "wires 310 and 330") are twisted together. Specifically, the specific twisted wire 300X includes one core wire 310 and six of the side wires 330 arranged around the core wire 310. The wires 310 and 330 each have a substantially circular shape in the transverse cross section of the proximal end portion BP. In the transverse cross section of the proximal end portion BP, the core wire 310 and the side wires 330 abut against each other, and adjacent ones of the side wires 330 abut against each other. More specifically in the side wires 330, there is no gap between adjacent ones of the side wires 330. A diameter D1 of each side wire 330 is, for example, from about 0.01 to 0.1 mm. The wires 310 and 330 are examples of a wire in the claims.

As illustrated in FIG. 2, specifically the side wires 330 configuring the specific twisted wire 300X include an outermost wire 331, a first outer wire 332, a second outer wire 333, a first inner wire 334, a second inner wire 335, and an innermost wire 336. The outermost wire 331 is a wire positioned farthest from a center point O of the core shaft 10 in the radial direction RD, out of the six side wires 330. In other words, the outermost wire 331 is a wire having the longest distance from the center point O of the core shaft 10, out of the six side wires 330. For example, a distance between the outermost wire 331 and the center point O of the core shaft 10 is a distance between the center point O and an intersection point PO of the outermost wire 331, in a virtual straight line VL passing through the center point O of the core shaft 10. The intersection point PO of the outermost wire 331 is an intersection point having a longer distance from the center point O, out of the intersection points with the virtual straight line VL and an outer edge of the outermost wire 331. The innermost wire 336 is a wire being positioned closest to the center point O of the core shaft 10 in the radial direction RD, out of the six side wires 330, and having a shortest distance from the center point O. The outer wires 332 and 333 are wires adjacent to the outermost wire 331, and the inner wires 334 and 335 are wires adjacent to the innermost wire 336. The outer wires 332 and 333 and the inner wires 334 and 335 are adjacent to each other. In the transverse cross section of the proximal end portion BP illustrated in FIG. 2, an outer peripheral surface SO of the coil body 30 is configured of the five wires 331, 332, 333, 334, and 335, and an inner peripheral surface SI of the coil body 30 is configured of the three wires 334, 335, and 336. In the transverse cross section of the proximal end portion BP, a cross-sectional area A1 of the outermost wire 331 configuring the specific twisted wire 300X is substantially equal in size to each of cross-sectional areas of each of the other wires 332, 333, 334, 335, and 336. The outermost wire 331 is an example of an outermost wire in the claims.

With reference to FIG. 3, the transverse cross section of the specific twisted wire 300X at the distal end portion AP will be described. A of FIG. 3 illustrates a transverse cross section of the specific twisted wire 300X in the proximal end side of the diminishing portion DP, B of FIG. 3 illustrates a transverse cross section of the specific twisted wire 300X at the distal end side of the diminishing portion DP, and C of FIG. 3 illustrates a transverse cross section of the specific twisted wire 300X in the flat portion FP. The specific twisted wire 300X is configured of the outermost wire 331, the first outer wire 332, the second outer wire 333, the first inner wire 334, the second inner wire 335, and the innermost wire 336 also in the diminishing portion DP and the flat portion FP, similarly to the proximal end portion BP.

As illustrated in A to C of FIG. 3, the outermost wire 331 in the diminishing portion DP and the flat portion FP has a shape in which a part of the outer peripheral side of the coil body 30 is missing, as compared to the outermost wire 331 at the proximal end portion BP. That is, lengths Da, Db, and Dc (lengths in the radial direction RD) of the outermost wire 331 in the diminishing portion DP and the flat portion FP are all shorter than a diameter D1 of the outermost wire 331 at the proximal end portion BP. Therefore, lengths DA, DB, and DC of the specific twisted wire 300X in the diminishing portion DP and the flat portion FP are all shorter than the outer diameter DF of the specific twisted wire 300X at the proximal end portion BP. In other words, cross-sectional areas A1*a*, A1*b*, and A1*c* of the outermost wire 331 in the diminishing portion DP and the flat portion FP are all smaller than the cross-sectional area A1 of the outermost wire 331 at the proximal end portion BP, and further, the cross-sectional areas of the specific twisted wire 300X in the diminishing portion DP and the flat portion FP are smaller than the cross-sectional area of the specific twisted wire 300X in the proximal end portion BP.

The length of the outermost wire 331 in the diminishing portion DP continuously decreases from the proximal end side toward the distal end side (see FIGS. 1 and 2), as represented by the lengths Da and Db. In other words, the cross-sectional area of the outermost wire 331 in the diminishing portion DP continuously decreases from the proximal end side to the distal end side, as represented by the cross-sectional areas A1*a* and A1*b*. The length Dc of the outermost wire 331 in the flat portion FP is smaller than the length of the distal end side of the diminishing portion DP (for example, the length Db), and is substantially constant across the proximal end side and the distal end side. In other words, the cross-sectional area A1*c* of the outermost wire 331 in the flat portion FP is smaller than the cross-sectional area (for example, the cross-sectional area A1*b*) of the distal end side of the diminishing portion DP, and is substantially constant across the proximal end side and the distal end side.

In the diminishing portion DP and the flat portion FP, an outermost surface S31 of the outermost wire 331 has a flat shape. The outermost surface S31, out of surfaces configuring the outermost wire 331, is a surface located at the outermost peripheral side in the radial direction RD, and is a surface configuring a part of the outer peripheral surface SO of the coil body 30. In the diminishing portion DP and the flat portion FP, a surface roughness of the outermost surface S31 of the outermost wire 331 is higher than a surface roughness of an inner peripheral surface of the innermost wire 336 (the inner peripheral surface SI of the coil body 30).

In the present embodiment, the specific twisted wire 300X in the diminishing portion DP and the flat portion FP includes the outermost wire 331 and the side wires 330 in which a part of the outer peripheral side of the coil body 30 is missing. For example, as illustrated in FIG. 3(A), at the proximal end side of the diminishing portion DP, the cross-sectional areas of the outer wires 332 and 333 are smaller than the cross-sectional area of the outer wires 332 and 333 at the proximal end portion BP, respectively. As illustrated in B I and C in FIG. 3, in the distal end side of the diminishing portion DP and the flat portion FP, in addition to the outer wires 332 and 333, the inner wires 334 and 335 also have smaller cross-sectional areas than the cross-sectional areas of the inner wires 334 and 335 at the proximal end portion BP. It is noted that a change in cross-sectional area in the diminishing portion DP and the flat portion FP in the outer wires 332 and 333 and the inner wires 334 and 335 is similar to a change in cross-sectional area of the outermost wire 331. That is, in the diminishing portion DP, the cross-sectional areas of the outer wires 332 and 333 and the inner wires 334 and 335 continuously decrease from the proximal end side toward the distal end side, and in the flat portion FP, such cross-sectional areas are substantially constant across the proximal end side and the distal end side. The outermost surfaces of the outer wires 332 and 333 and the inner wires 334 and 335 are also flat, and the surface roughness of the outermost surfaces is higher than the surface roughness of the inner peripheral surface of the innermost wire 336 (the inner peripheral surface SI of the coil body 30). The cross-sectional areas of the core wire 310 and the innermost wire 336 in the diminishing portion DP and the flat portion FP are substantially the same as the cross-sectional areas of the core wire 310 and the innermost wire 336 at the proximal end portion BP, respectively.

As illustrated in B and C of FIGS. 3, in the distal end side of the diminishing portion DP and the flat portion FP, a gap SP is provided between the outermost wire 331 and the outer wires 332 and 333. Similarly the gap SP is provided between the outer wires 332 and 333 and the inner wires 334 and 335. In the present embodiment, a size of the gap SP in the flat portion FP is larger than a size of the gap SP at the distal end side of the diminishing portion DP. Here, "the gap SP is provided" means that adjacent ones of the wires do not abut against each other.

An example of a method of manufacturing the coil body 30 in the guide wire 100 is described below. That is, the core wire 310 and the six side wires having the shape of the innermost wire 336 are twisted together to produce a twisted wire (hereinafter referred to as "unprocessed twisted wire").

Next, a description of how to make the coil body 30 is provided. First, an unprocessed coil body is produced. The unprocessed coil body may be produced, for example, by winding a plurality of (eight in the present embodiment) unprocessed twisted wires around a metal core to obtain a coil shape, and then, removing the metal core and cutting the obtained coil body to a predetermined length.

Next, the coil body 30 is produced. For example, the coil body 30 may be produced by immersing one end portion of the unprocessed coil body (a portion of the coil body 30 where the distal end portion AP (the diminishing portion DP and the flat portion FP) is formed) into an electrolyte, and reducing a diameter of such an end portion by electropolishing. Strictly speaking, the shape of the diminishing portion DP and the flat portion FP may be adjusted by adjusting an electropolishing parameter to adjust an amount of polishing. Examples of the electropolishing parameter include a liquid temperature of an electrolyte, a viscosity an electric current value, and a removal speed when the unprocessed coil body is removed from the electrolyte. By the manufacturing method described above, the coil body 30 having the configuration described above is manufactured.

The surface roughness of the outermost surface S31 of the outermost wire 331 of the twisted wires 300 configuring the coil body 30 may be increased by increasing the electric current value during electropolishing, for example.

A-3. Effects of First Embodiment

As described above, the guide wire 100 of the present embodiment incudes the core shaft 10, and the coil body 30 configured of the twisted wires 300 obtained by twisting the wires 310 and 330 together, the coil body 30 arranged to surround the outer periphery of the core shaft 10. The coil body 30 includes the distal end portion AP and the proximal end portion BP. The outer diameter DE of the coil body 30 at the distal end portion AP is smaller than the outer diameter DE of the coil body 30 at the proximal end portion BP. The cross-sectional areas A1*a*, A1*b*, and A1*c* of the outermost wire 331 in the transverse cross section of the coil body 30 at the distal end portion AP are smaller than the cross-sectional area A1 of the outermost wire 331 in the transverse cross section of the coil body 30 at the proximal end portion BP. The inner diameter DI of the coil body 30 is constant.

When the cross-sectional area of the coil body in the transverse cross section of the guide wire is smaller, the flexibility is improved. In the guide wire 100 of the present embodiment, the inner diameter DI of the coil body 30 is constant, and the outer diameter DE of the coil body 30 at the distal end portion AP is smaller than the outer diameter DE of the coil body 30 at the proximal end portion BP. In other words, in the transverse cross section of the guide wire 100, the cross-sectional area of the coil body 30 at the distal end portion AP is smaller than the cross-sectional area of the coil body 30 at the proximal end portion BP. Therefore, as compared to the proximal end portion BP, the flexibility of the coil body 30 at the distal end portion AP may be improved, thereby improving the flexibility of the guide wire.

The rotational performance of the guide wire is improved as the diameter of each wire of the twisted wire configuring the coil body is increased. In the guide wire 100 of the present embodiment, in the transverse cross section of the coil body 30 at the distal end portion AP, the cross-sectional areas A1*a*, A1*b*, and A1*c* of the outermost wire 331 configuring the twisted wire 300 (the specific twisted wire 300X) are smaller than the cross-sectional area A1 of the outermost wire 331 in the transverse cross section of the coil body 30 at the proximal end portion BP. That is, in the guide wire 100 of the present embodiment, the outer diameter DE of the coil body 30 may be decreased without evenly decreasing the diameter of a particular wire configuring the coil body across the entire coil body. Therefore, deterioration of the rotational performance of the guide wire 100 may be reduced. In the guide wire 100 of the present embodiment, when the inner diameter DI of the coil body 30 is maintained constant, the inner cavity H formed between the core shaft 10 and the coil body 30 may be secured. Therefore, according to the guide wire 100 of the present embodiment, the inner cavity H formed between the core shaft 10 and the coil body 30 is secured, and at the same time, a good flexibility of the distal end portion of the guide wire 100 may be maintained and the rotational performance may be improved.

In the guide wire 100 of the present embodiment, the twisted wire 300 (specific twisted wire 300X) is configured of the core wire 310 and a plurality of the side wires 330. The core wire 310 surrounded by the side wires 330 does not configure the outer peripheral surface SO over the entire coil body 30, and thus, the core wire 310 has a constant diameter over the entire coil body 30. In other words, the core wire 310 is not deformed over the entire coil body 30. This allows the core wire 310 to contribute to improvement of the rotational performance of the guide wire 100 over the entire coil body 30. In the guide wire 100 of the present embodiment, the innermost wire 336 configuring the twisted wire 300 (the specific twisted wire 300X) has a constant diameter over the entire proximal end portion BP and the entire distal end portion AP. This allows the innermost wire 336 to contribute to improvement of the rotational performance of the guide wire 100 over the entire coil body 30. Therefore, according to the guide wire 100 of the present embodiment, the rotational performance of the guide wire 100 may be effectively improved.

In the guide wire 100 of the present embodiment, in the transverse cross section of the coil body 30 at the distal end portion AP, the outermost wire 331 configuring the distal end portion AP includes the gap SP between the adjacent wires (the outer wires 332 and 333). To improve the operability of the guide wire in a complicatedly curved blood vessel, there is a case where the guide wire is used by using a fingertip or an instrument (a shape needle, for example) to bend the distal end portion of the guide wire, or to return such a distal end portion to the original shape after use (hereinafter, referred to as "shape and reshape"). Thus, the distal end portion of the guide wire may be required to be easily shaped and reshaped. In the guide wire 100 of the present embodiment, the outermost wire 331 configuring the distal end portion AP includes the gap SP between the adjacent wires (the outer wires 332 and 333). Thus, as compared to a configuration having no gap, interference of the wires may be prevented, allowing the ease shaping and reshaping the coil body 30 at the distal end portion AP and the flexibility at the distal end portion AP to be improved. Therefore, according to the guide wire 100 of the present embodiment, the ease of shaping and reshaping guide wire 100 and the flexibility of the guide wire 100 may be improved.

In the guide wire 100 of the present embodiment, in the transverse cross section of the coil body 30 at the distal end portion AP, the outermost surface S31 of the surfaces configuring the outermost wire 331 has a flat shape. In other words, in the guide wire 100 of the present embodiment, the flat surface (the outermost surface S31) is provided in the outer peripheral surface SO of the guide wire 100 at the distal end portion AP. Thus, as compared to a configuration where the outer peripheral surface (the outermost surface of the outermost wire) has an arc shape, it is possible to ensure that the fingertip or the instrument (the shape needle, for example) is in surface contact with the flat surface of the outer peripheral surface, and the ease of the shaping and reshaping of the coil body 30 at the distal end portion AP may be improved. Therefore, according to the guide wire 100 of the present embodiment, the ease of the shaping and reshaping of the guide wire 100 may be more effectively improved.

In the guide wire 100 of the present embodiment, at the side of the proximal end portion BP, the distal end portion AP includes the diminishing portion DP in which a cross-sectional area (for example, the cross-sectional areas A1*a* and A1*b*) of the outermost wire 331 continuously decreases in size from the side of the proximal end portion BP to the distal end. In the guide wire 100 of the present embodiment, the stiffness of the coil body 30 gradually decreases in the diminishing portion DP at the distal end portion AP. According to the guide wire 100 of the present embodiment, the diminishing portion DP is included at the proximal end portion BP side at the distal end portion AP, and thus, deterioration of the rotational performance features such as torqueability and rotation followability, which is caused due to the sudden change in stiffness between the distal end portion AP and the proximal end portion BP, may be suppressed.

In the guide wire 100 of the present embodiment, the proximal end portion BP and the distal end portion AP of the coil body 30 are integrally formed. In a configuration where the proximal end portion of the coil body and the feature portion are joined by a joint portion, the rotational force transmitted from the proximal end portion is not smoothly transmitted to the feature portion, and due to a residual stress in the joint portion, rotational performance features such as torqueability and rotation followability deteriorate. On the other hand, according to the guide wire 100 of the present embodiment, the proximal end portion BP and the distal end portion AP of the coil body 30 are integrally formed, smooth transmission of the rotational force from the proximal end portion BP to the distal end portion AP may be realized, thereby improving the rotational performance of the guide wire 100.

In the guide wire 100 of the present embodiment, the surface roughness of the outermost surface S31 of the outermost wire 331 at the distal end portion AP is higher than the surface roughness of the inner peripheral surface SI of the coil body 30 at the distal end portion AP. According to the guide wire 100 of the present embodiment, the surface area of the outer peripheral surface SO of the coil body 30 increases, improving adhesion between the outer peripheral surface SO and the resin portion 50 and suppressing peeling of the resin portion 50 from the coil body 30 and the like.

B. Second Embodiment

Figure 4:
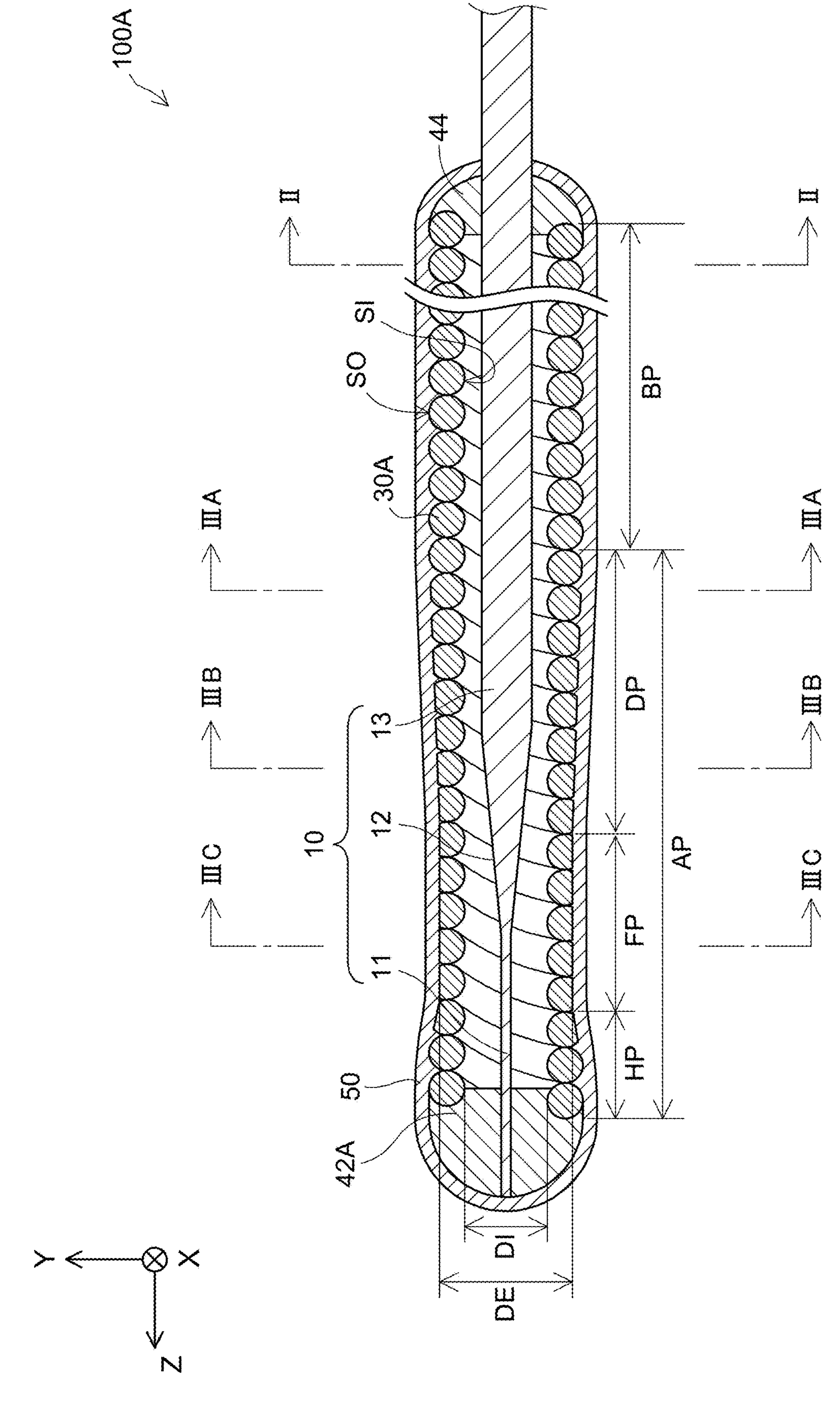
FIG. 4 is an explanatory diagram schematically illustrating a configuration of a guide wire 100A in a second embodiment.

FIG. 4 is an explanatory diagram schematically illustrating a configuration of a guide wire 100A in a second embodiment. FIG. 4 illustrates a configuration of a longitudinal cross section (YZ cross section) of the guide wire 100A. Below, a configuration the same as that of the guide wire 100 of the first embodiment described above out of the configuration of the guide wire 100A of the second embodiment will be referred to by the same reference numerals, and description thereof will be omitted where appropriate.

The guide wire 100A of the second embodiment includes the core shaft 10, a coil body 30A, a distal end side joint portion 42A, the proximal end side joint portion 44, and the resin portion 50. The guide wire 100A differs from the guide wire 100 of the first embodiment in that the former includes the coil body 30A instead of the coil body 30 of the first embodiment.

The coil body 30A is a coil-shaped member formed into a hollow cylindrical shape by winding a plurality of twisted wires into a spiral shape, similarly to the coil body 30 of the first embodiment, and is arranged to surround the outer periphery of the core shaft 10. The coil body 30A includes the proximal end portion BP and the distal end portion AP including the distal end of the coil body 30. Also in the present embodiment, each of the plurality of twisted wires configuring the coil body 30A is continuous from the proximal end portion BP to the distal end portion AP. In other words, the proximal end portion BP and the distal end portion AP are integrally formed. A material for forming the coil body 30A is similar to the material of the coil body 30. The coil body 30A is an example of a twisted wire coil body in the claims.

In the coil body 30A, the distal end portion AP includes the diminishing portion DP, the flat portion FP, and a head portion HP. The diminishing portion DP is a portion that continues to the proximal end portion BP, and the flat portion FP is a portion that continues to the diminishing portion DP at one end portion and continues to the head portion HP at the other end portion. The head portion HP is a portion that continues to the flat portion FP and that includes a distal end of the coil body 30A. Similarly to the coil body 30 of the first embodiment, in the diminishing portion DP, the outer diameter DE of the coil body 30A continuously decreases in size from the proximal end side toward the distal end side, and in the flat portion FP, such an outer diameter DE is substantially constant across the proximal end side and the distal end side. That is, the outer diameter DE at the proximal end side of the diminishing portion DP is equivalent to the outer diameter DE at the distal end side of the proximal end portion BP, and the outer diameter DE at the proximal end side of the flat portion FP is equivalent to the outer diameter DE at the distal end side of the diminishing portion DP. In other words, the outer diameter DE of the coil body 30A in the diminishing portion DP and the flat portion FP is smaller than the outer diameter DE of the coil body 30A at the proximal end portion BP. On the other hand, the inner diameter DI of the coil body 30 is substantially constant over both the proximal end portion BP and the distal end portion AP. The flat portion FP and the diminishing portion DP are examples of a feature portion in the claims, and the diminishing portion DP is an example of "a portion where a cross-sectional area of an outermost wire continuously decreases from a side of a proximal end portion to a distal end" in the claims.

In the head portion HP, the outer diameter DE of the coil body 30A is larger than the outer diameter DE of the flat portion FP, and at the distal end side of the head portion HP, the outer diameter DE of the coil body 30A is equivalent to the outer diameter DE of the proximal end portion BP. The outer diameter DE at the proximal end side of the head portion HP is equivalent to the outer diameter DE at the distal end side of the flat portion FP. The head portion HP is an example of a distal end portion in the claims.

In the present embodiment, the distal end side joint portion 42A is a member that joins the distal end of the core shaft 10 and the distal end of the distal end portion AP (specifically the head portion HP) of the coil body 30. That is, the distal end of the core shaft 10 and the distal end of the distal end portion AP of the coil body 30 are tightly fixed to be embedded into the distal end side joint portion 42A.

The guide wire 100A according to the second embodiment and including the above-described configuration also exhibits an effect similar to that of the first embodiment. In the present embodiment, none of the wires configuring the coil body 30A is deformed at the distal end side of the head portion HP of the coil body 30A. Therefore, in the coil body 30A of the present embodiment, untwisting of the twisted wires configuring the coil body 30A may be suppressed.

C. Modifications

The technique disclosed herein is not limited to the above-described embodiments and the modification, and may be modified into various modes without departing from the spirit of the above-described embodiments and the modification. For example, the following modifications can also be applied.

Figure 5:
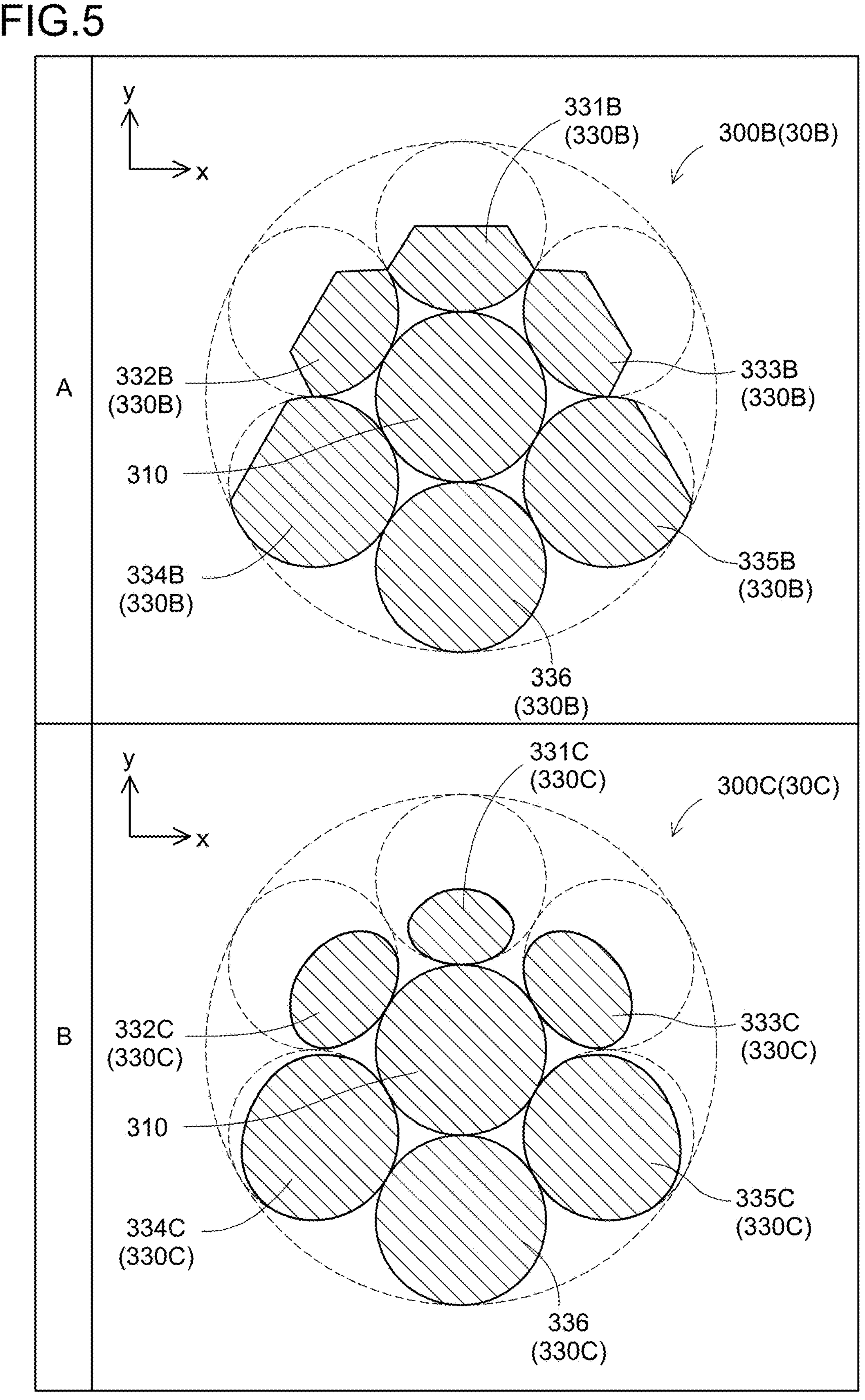
FIG. 5 is an explanatory view schematically illustrating XY cross-sectional configurations of one twisted wire 300B of a coil body 30B and one twisted wire 300C of a coil body 30C configuring a guide wire of a modification.

In the above-described embodiments, as illustrated in B and C of FIG. 3, the configuration is such that the gap SP is provided between the outermost wire 331 and the outer wires 332 and 333, however, this is not limiting. A of FIG. 5 schematically illustrates an XY cross-sectional configuration of twisted wires 300B (including side wires 330B) configuring the coil body 30B at the same position as C of FIG. 3 (position of IIIC-IIIC in FIG. 1). As illustrated in A of FIG. 5, a configuration may be employed where an outermost wire 331B and outer wires 332B and 333B abut against each other, i.e., where the twisted wires 300B do not include the gap SP therebetween. Also in such a configuration, the outer diameter DE of the coil body 30B at the distal end portion AP may be smaller than the outer diameter DE of the coil body 30B at the proximal end portion BP, and the inner diameter DI of the coil body 30B may be constant. Each of cross-sectional areas of wires 331B, 332B, 333B, 334B, and 335B in a transverse cross section of the coil body 30B at the distal end portion AP is smaller than the cross-sectional area of each wire at the proximal end portion BP. Therefore, even in such a configuration, effects similar to that in the above-described embodiments may be obtained.

In the above-described embodiments, as illustrated in A to C of FIG. 3, the configuration is such that the outermost surface S31 of the outermost wire 331 has a flat shape, however, this is not limiting. B of FIG. 5 schematically illustrates an XY cross-sectional configuration of twisted wires 300C (including side wires 330C) configuring the coil body 30C at the same position as in C of FIG. 3 (position of IIIC-IIIC in FIG. 1). As illustrated in B of FIG. 5, a configuration where outermost surfaces of wires 331C, 332C, 333C, 334C, and 335C configuring the twisted wires 300C have an arc shape may be employed. Also in such a configuration, the outer diameter DE of the coil body 30C at the distal end portion AP may be smaller than the outer diameter DE of the coil body 30C at the proximal end portion BP, and the inner diameter DI of the coil body 30C may be constant. Each of cross-sectional areas of the wires 331C, 332C, 333C, 334C, and 335C in a transverse cross section of the coil body 30C at the distal end portion AP is smaller than the cross-sectional area of each wire at the proximal end portion BP. Therefore, even in such a configuration, a similar effect to that in the above-described embodiments may be obtained.

In the above embodiments, the coil body 30 has a configuration formed by tightly winding the twisted wires 300 obtained by twisting the core wire 310 and the six side wires 330 together. However, the configuration may be such that the twisted wires 300 are loosely wound at the proximal end portion BP and/or the distal end portion AP of the coil body 30. In the above-described embodiments, the configuration is such that the coil body 30 is formed into a hollow cylindrical shape by winding the eight twisted wires 300 into a spiral shape. However, the configuration may be such that the coil body 30 is formed into a hollow cylindrical shape by winding the one twisted wire 300 into a spiral shape, or the configuration may be such that the coil body 30 is formed into a hollow cylindrical shape by winding two to seven of the twisted wires 300 or nine or more of the twisted wires 300 into a spiral shape. Such configurations are not limiting as long as the number of wires configuring the twisted wire is two or more. For example, the configuration may be such that one to five or seven or more side wires are used, and the configuration may be such that the twisted wire does not include the core wire.

In the guide wire 100 of the above-described embodiments, a configuration not including the resin portion 50 and a configuration including a resin portion in a part thereof may be adopted, for example.

In the guide wire 100 of the above-described embodiments, the proximal end portion BP and the distal end portion AP configuring the coil body 30 may be formed separately. The proximal end portion BP and the distal end portion AP may be joined by a joint portion or the like. A well-known material may be used as a material configuring the joint portion, and for example, a brazing material (such as aluminum alloy brazing, silver brazing, and gold brazing), metal solder (such as Ag—Sn alloy and Au—Sn alloy), an adhesive (such an epoxy-based adhesive), and the like may be used.

In the above-described embodiments, all the twisted wires 300 configuring the coil body 30 are configured in much the same way as the specific twisted wire 300X, but this is not limiting, and a part of the twisted wires 300 may not be configured in much the same way as the specific twisted wire 300X.

In the above-described embodiments, the configuration where the outermost surface S31 of the outermost wire 331 has a flat shape in the transverse cross section of the coil body 30 at the distal end portion AP is adopted, but this is not limiting, and the outermost surface of the outermost wire may have a shape such as an arc shape. The configuration may be such that the surface roughness of the outermost surface S31 of the outermost wire 331 is equivalent to the surface roughness of the inner peripheral surface SI of the coil body 30 at the distal end portion AP, or the surface roughness of the inner peripheral surface SI is higher than the surface roughness of the outermost surface S31.

In the above embodiments, a member capable of imparting various performances may be provided in the inner cavity H formed between the core shaft 10 and the coil body 30. Examples of such a member include an X-ray opaque member, a member capable of improving the rotational performance, an auxiliary member capable of improving shapeability, and a member capable of improving safety. When the X-ray opaque member is arranged at the distal end portion of the inner cavity H, the visibility in X-ray fluoroscopy and the operability by an operator may be improved. Examples of the X-ray opaque member include a single coil, a twisted wire coil, or a pipe formed of platinum, tungsten, or the like. Examples of the member capable of improving the rotational performance include a coil body and a twisted wire coil body. Examples of the auxiliary member capable of improving the shapeability include stainless steel and a wire rod formed of annealed NiTi. Examples of the member capable of improving the safety include a twisted wire body formed of stainless steel. When the twisted wire body formed of stainless steel, the tensile strength of the guide wire may be ensured.

In each of the above embodiments, the core shaft 10 is configured of the small diameter portion 11, the tapered portion 12, and the large diameter portion 13, but the shape of the core shaft 10 is not particularly limited, and the core shaft 10 may not include at least one of these three portions and may include another portion in addition to these three portions. For example, in the core shaft 10, the proximal end side of the large diameter portion 13 may be connected to a portion having a larger diameter than the large diameter portion 13.

The material of each member in the above-described embodiment is merely an example and various modifications can be applied. The method of manufacturing the coil body in each of the above-described embodiments is merely an example, and various modifications are possible. For example, in the above-described embodiments, the coil body 30 may be produced from an unprocessed coil body by chemical processing other than electropolishing and physical processing such as grinding and polishing.

The present aspect has been described above based on the embodiments and the modifications; however, the embodiments according to the above aspects are provided to facilitate understanding of the present aspect and not to limit the aspect. In some instances, as would be apparent to one of skill in the art as of the filing of the present application, features, characteristics, and/or elements described in connection with a particular embodiment may be used singly or in combination with features, characteristics, and/or elements described in connection with other embodiments unless otherwise indicated. The present aspect may be modified and improved without departing from the spirit thereof and the scope of claims, and the present aspect includes equivalents thereof. Furthermore, the technical features may be omitted as appropriate unless they are described as essential in this description.

DESCRIPTION OF REFERENCE NUMERALS

10: Core shaft
11: Small diameter portion
12: Tapered portion
13: Large diameter portion
30: Coil body
30A: Coil body
30B: Coil body
30C: Coil body
42: Distal end side joint portion
42A: Distal end side joint portion
44: Proximal end side joint portion
50: Resin portion
100: Guide wire
100A: Guide wire
300: Twisted wire
300B: Twisted wire
300C: Twisted wire
300X: Specific twisted wire

310: Core wire
330: Side wire
331: Outermost wire
331B, 332B, 333B, 334B, 335B: Wire
331B: Outermost wire
331C, 332C, 333C, 334C, 335C: Wire
332: First outer wire
332A, 333A: Outer wire
333: Second outer wire
334: First inner wire
335: Second inner wire
336: Innermost wire
A1: Cross-sectional area
A1*a*, A1*b*, A1*c*: Cross-sectional area
AP: Distal end portion
BP: Proximal end portion
D1: Diameter
DA, DB, DC: Length
DE: Outer diameter
DF: Outer diameter
DI: Inner diameter
DP: Diminishing portion
Da, Db, Dc: Length
FP: Flat portion
H: Inner cavity
HP: Head portion
IC: Inscribed circle
O: Center point
OC: Circumscribed circle
PO: Intersection point
RD: Radial direction
S31: Outermost surface
SI: Inner peripheral surface
SO: Outer peripheral surface
SP: Gap
VL: Virtual straight line

The invention claimed is:

1. A guide wire comprising:
a core shaft; and
a twisted wire coil body including a plurality of wires twisted together and arranged along an outer periphery of the core shaft, the twisted wire coil body including a distal end portion including a distal and a feature portion, and a proximal end portion, wherein
an outer diameter of the twisted wire coil body in the feature portion is smaller than an outer diameter of the twisted wire coil body at the proximal end portion,
a cross-sectional area of an outermost wire being a wire having a longest distance to a center point of the core shaft, out of the plurality of wires, in a transverse cross section of the twisted wire coil body in the feature portion, is smaller than a cross-sectional area of the wire having a longest distance to the center point of the core shaft, out of the plurality of wires, in a transverse cross section of the twisted wire coil body at the proximal end portion,
an inner diameter of the twisted wire coil body is constant,
wherein in at least one transverse cross section of the twisted wire coil body in the feature portion, the outermost wire forming the feature portion has a gap with an adjacent one of the plurality of wires; and
wherein each of the plurality of wires twisted together includes a core wire and a plurality of side wires twisted around the core wire, and wherein a diameter of the core wire is constant throughout the feature portion and the proximal end portion.

2. The guide wire according to claim 1, wherein an outermost surface among surfaces configuring the outermost wire in the transverse cross section of the twisted wire coil body in the feature portion is flat.

3. The guide wire according to claim 2, wherein the feature portion includes, at a side of the proximal end portion, a portion where the cross-sectional area of the outermost wire continuously decreases in size toward the distal end from the side of the proximal end portion.

4. The guide wire according to claim 3, wherein the proximal end portion and the feature portion of the twisted wire coil body are integrally formed.

5. The guide wire according to claim 4, wherein a surface roughness of the outermost surface of the outermost wire in the feature portion is higher than a surface roughness of an inner peripheral surface of the twisted wire coil body in the feature portion.

6. The guide wire according to claim 2, wherein a surface roughness of the outermost surface of the outermost wire in the feature portion is higher than a surface roughness of an inner peripheral surface of the twisted wire coil body in the feature portion.

7. The guide wire according to claim 2, wherein the plurality of wires includes a first outer wire adjacent to the outermost wire, and wherein an outermost surface of the first outer wire in the transverse cross section of the twisted wire coil body in the feature portion is flat.

8. The guide wire according to claim 1, wherein the feature portion includes, at a side of the proximal end portion, a portion where the cross-sectional area of the outermost wire continuously decreases in size toward the distal end from the side of the proximal end portion.

9. The guide wire according to claim 1, wherein the proximal end portion and the feature portion of the twisted wire coil body are integrally formed.

10. The guide wire according to claim 1, wherein a surface roughness of the outermost surface of the outermost wire in the feature portion is higher than a surface roughness of an inner peripheral surface of the twisted wire coil body in the feature portion.

11. The guide wire according to claim 1, wherein the feature portion is at the distal end of the twisted wire coil body.

12. The guide wire according to claim 1, wherein the feature portion includes, at a side of the proximal end portion, a diminishing portion where the cross-sectional area of the outermost wire continuously decreases in size toward the distal end from the side of the proximal end portion, and at a side of the distal end portion, a fixed portion where the cross-sectional area of the outermost wire has a fixed diameter of an outer diameter of the diminishing portion.

13. The guide wire according to claim 12, wherein the fixed portion is at the distal end of the twisted wire coil body.

14. The guide wire according to claim 12, wherein the cross-sectional area of the outermost wire in the diminishing portion continuously decreases from a size in the proximal end portion to the fixed portion.

15. The guide wire according to claim 12, wherein the twisted wire coil body includes a head portion at the distal end, the head portion having an outer diameter larger than the fixed portion.

16. The guide wire according to claim 15, wherein the head portion has an outer diameter equal to that of the proximal end portion.

17. The guide wire according to claim 12, wherein a size of the gap between the outermost wire and a circumferentially adjacent wire in the fixed portion is larger than a size of the gap in the diminishing portion.

18. The guide wire according to claim 1, wherein an outermost surface among surfaces configuring the outermost wire in the transverse cross section of the twisted wire coil body in the feature portion is curved.

19. The guide wire according to claim 1, wherein the feature portion includes a diminishing portion where the outer diameter continuously decreases and a flat portion distal to the diminishing portion where the outer diameter is constant, and wherein a size of the gap in the flat portion is larger than a size of the gap in the diminishing portion.

* * * * *